(12) United States Patent
Ketels et al.

(10) Patent No.: US 11,712,492 B2
(45) Date of Patent: Aug. 1, 2023

(54) SANITIZING CUP

(71) Applicant: Faurecia Interior Systems, Inc., Auburn Hills, MI (US)

(72) Inventors: Cedric Ketels, Mountain View, CA (US); Thomas Dessapt, Sunnyvale, CA (US)

(73) Assignee: Faurecia Interior Systems, Inc., Auburn Hills, MI (US)

( * ) Notice: Subject to any disclaimer, the term of this patent is extended or adjusted under 35 U.S.C. 154(b) by 359 days.

(21) Appl. No.: 16/949,403

(22) Filed: Oct. 28, 2020

(65) Prior Publication Data
US 2022/0125978 A1  Apr. 28, 2022

(51) Int. Cl.
*A61L 2/26* (2006.01)
*A61L 2/00* (2006.01)
*A61L 2/10* (2006.01)

(52) U.S. Cl.
CPC ............. *A61L 2/26* (2013.01); *A61L 2/0088* (2013.01); *A61L 2/10* (2013.01); *A61L 2202/11* (2013.01); *A61L 2202/121* (2013.01); *A61L 2202/122* (2013.01); *A61L 2202/15* (2013.01)

(58) Field of Classification Search
CPC ...... A61L 2/26; A61L 2202/11; A61L 2/0088; A61L 2/10; A61L 2202/121; A61L 2202/122; A61L 2202/15
See application file for complete search history.

(56) References Cited

U.S. PATENT DOCUMENTS

| | | | |
|---|---|---|---|
| 8,602,257 B2 | 12/2013 | Godsell | |
| 8,809,806 B1 * | 8/2014 | Deese | A61L 2/0088 250/455.11 |
| 9,758,101 B2 | 9/2017 | Clair-Chalupka | |
| 10,499,774 B1 * | 12/2019 | Ryan | A47K 5/1205 |
| 2015/0122688 A1 * | 5/2015 | Dias | A47G 19/027 206/459.1 |
| 2018/0263432 A1 * | 9/2018 | Yang | A47K 5/1217 |
| 2018/0280554 A1 * | 10/2018 | Khajavi | A61L 2/10 |
| 2019/0076558 A1 | 3/2019 | Zhang-Miske et al. | |

FOREIGN PATENT DOCUMENTS

CN  110639036 A  *  1/2020

OTHER PUBLICATIONS

"Automatic Soap Dispenser," Amazon.com, accessed Oct. 28, 2020 at https://www.amazon.com/Automatic-Dispenser-Touchless-MaxLaxer-Hands-Free/dp/B087FCBTS1/ref=sxts_sxwds-bia-wc-drs1_0?crid=7MSPSZX55ZEN&cv_ct_cx=automatic+soap+dispenser&dchild=1&keywords=automatic+soap+dispense, 10 pages.

"UV CLEAN Portable Sanitizer Bag," homedics.com, accessed Oct. 28, 2020 at https://www.homedics.com/uv-clean-portable-sanitizer-bag/, 19 pages.

* cited by examiner

*Primary Examiner* — Sean E Conley
*Assistant Examiner* — Justin Hwang
(74) *Attorney, Agent, or Firm* — Reising Ethington P.C.

(57) ABSTRACT

A sanitizing cup that is advantageously used in a vehicle interior. The sanitizing cup includes a cup base and a sanitizing compartment extending at least partially from the cup base. The sanitizing compartment has a sanitizing area which can be used to sanitize an object, such as a user's face mask. The sanitizing cup also includes a hand sanitizer dispenser extending at least partially from the cup base, from the sanitizing compartment, or from both of the cup base and the sanitizing compartment. A combined hand and mask sanitizing cup provides enhanced in-vehicle disinfection capabilities.

14 Claims, 3 Drawing Sheets

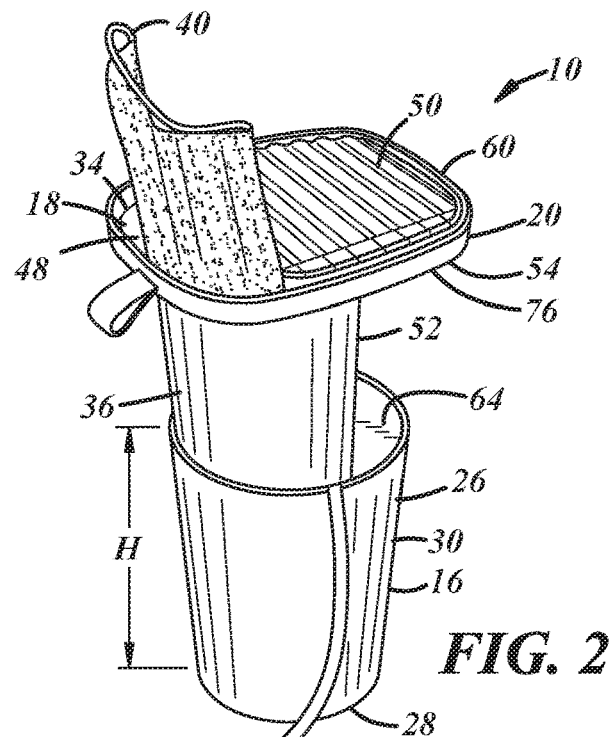
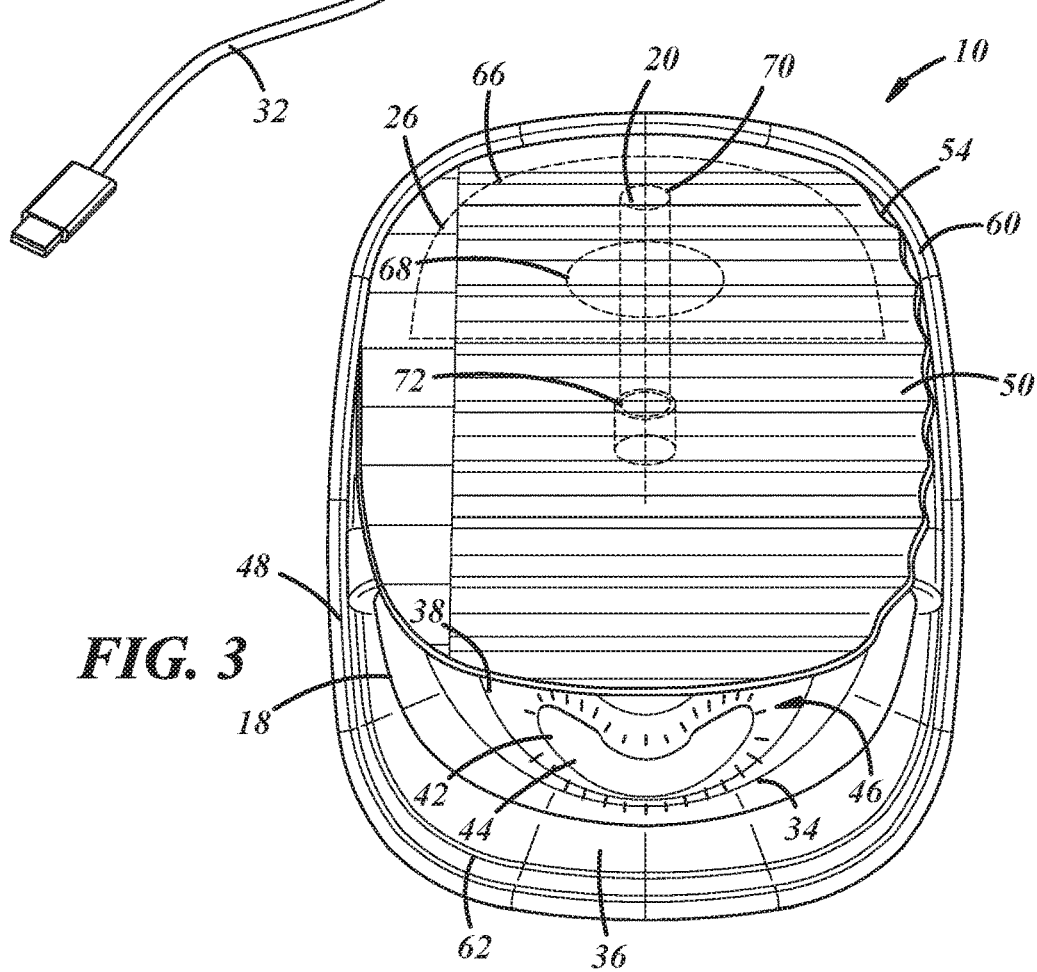

SANITIZING CUP

TECHNICAL FIELD

The present disclosure is related generally to sanitization, and more particularly, to a sanitizing cup for a vehicle interior.

BACKGROUND

When entering a vehicle, many vehicle users will sanitize their hands and remove their masks. Masks may be stored in random vehicle locations, such as in a cupholder, on a rear view mirror, or in other not so practical areas in the passenger cabin. A bottle of hand sanitizer may be used to disinfect a user's hands, which takes up additional storage space in the vehicle. Disinfecting devices such as the multifunctional hand sanitizer device disclosed in U.S. Pat. No. 8,602,257 and the ultraviolet-C (UVC) lights in US Patent Application Publication No. 2019/0076558 may separately enhance sanitization capabilities within the vehicle. However, given the non-integration of many disinfecting devices, they do not provide a streamlined storage solution that both enhances the sanitization capabilities while maximizing vehicle interior space.

SUMMARY

An illustrative sanitizing cup comprises a cup base and a sanitizing compartment extending at least partially from the cup base. The sanitizing compartment has a sanitizing area at least partially enclosed by a compartment wall. The sanitizing area is configured to store an object to be sanitized. The sanitizing cup further comprises a hand sanitizer dispenser extending at least partially from the cup base, the sanitizing compartment, or from both the cup base and the sanitizing compartment.

In various embodiments, the sanitizing compartment includes an ultraviolet-C (UVC) light source.

In various embodiments, the ultraviolet-C (UVC) light source is configured to form a U-shaped light distribution coming from the compartment wall.

In various embodiments, the compartment wall is a sidewall so light from the ultraviolet-C (UVC) light source is configured to be directed more toward a sanitizer backing wall opposite the sidewall.

In various embodiments, the compartment wall is a bottom wall so light from the ultraviolet-C (UVC) light source is configured to be directed more toward an opening in the sanitizing compartment opposite the bottom wall.

In various embodiments, the sanitizing area is at least partially U-shaped and configured to store a mask as the object to be sanitized.

In various embodiments, a height of the cup base is configured to be greater than a depth of a vehicle cup holder.

In various embodiments, the cup base is integrally built into an interior panel for a vehicle.

In various embodiments, a reservoir for hand sanitizer is located in the cup base.

In various embodiments, the hand sanitizer dispenser includes a drip wall, a sanitizer backing wall, and an overhanging dispensing wall.

In various embodiments, a nozzle and a sensor are located on the overhanging dispensing wall, and the sensor is configured to detect a user's hand and dispense sanitizer via the nozzle.

In various embodiments, there is a sanitization status indicator configured to indicate a sanitizing status relating to the object to be sanitized.

In various embodiments, there is a cup lid configured to at least partially enclose the sanitizing area.

In various embodiments, the cup lid is configured to slide between an open state in which the cup lid is situated over an overhanging dispensing wall and a closed state in which the cup lid is situated over an opening in the sanitizing compartment.

In various embodiments, the cup lid is configured to automatically transition between the open state and the closed state upon completion of a sanitization cycle.

It is contemplated that any number of the individual features of the above-described embodiments and of any other embodiments depicted in the drawings or description below can be combined in any combination to define an invention, except where features are incompatible.

BRIEF DESCRIPTION OF THE DRAWINGS

Illustrative embodiments will hereinafter be described in conjunction with the following figures, wherein like numerals denote like elements, and wherein:

FIG. 2 illustrates the sanitizing cup of FIG. 1 with a mask located partially in the sanitizing compartment;

FIG. 3 illustrates the inside of the sanitizing compartment of the sanitizing cup of FIGS. 1 and 2;

DESCRIPTION OF ILLUSTRATIVE EMBODIMENTS

Described herein is a sanitizing cup that is advantageously used in a vehicle to increase disinfection capabilities while maximizing in-vehicle storage. The sanitizing cup is designed to efficiently fit in or be integrated within the vehicle cabin so that a user can efficiently sanitize his or her hands and an object such as a mask. Further, the sanitizing cup can provide a more practical and clean storage solution for a user's mask. Integrating a hand sanitizer dispenser with a mask sanitizer can provide a more compact storage solution while addressing a user's desire to disinfect within the vehicle.

Figure 1:
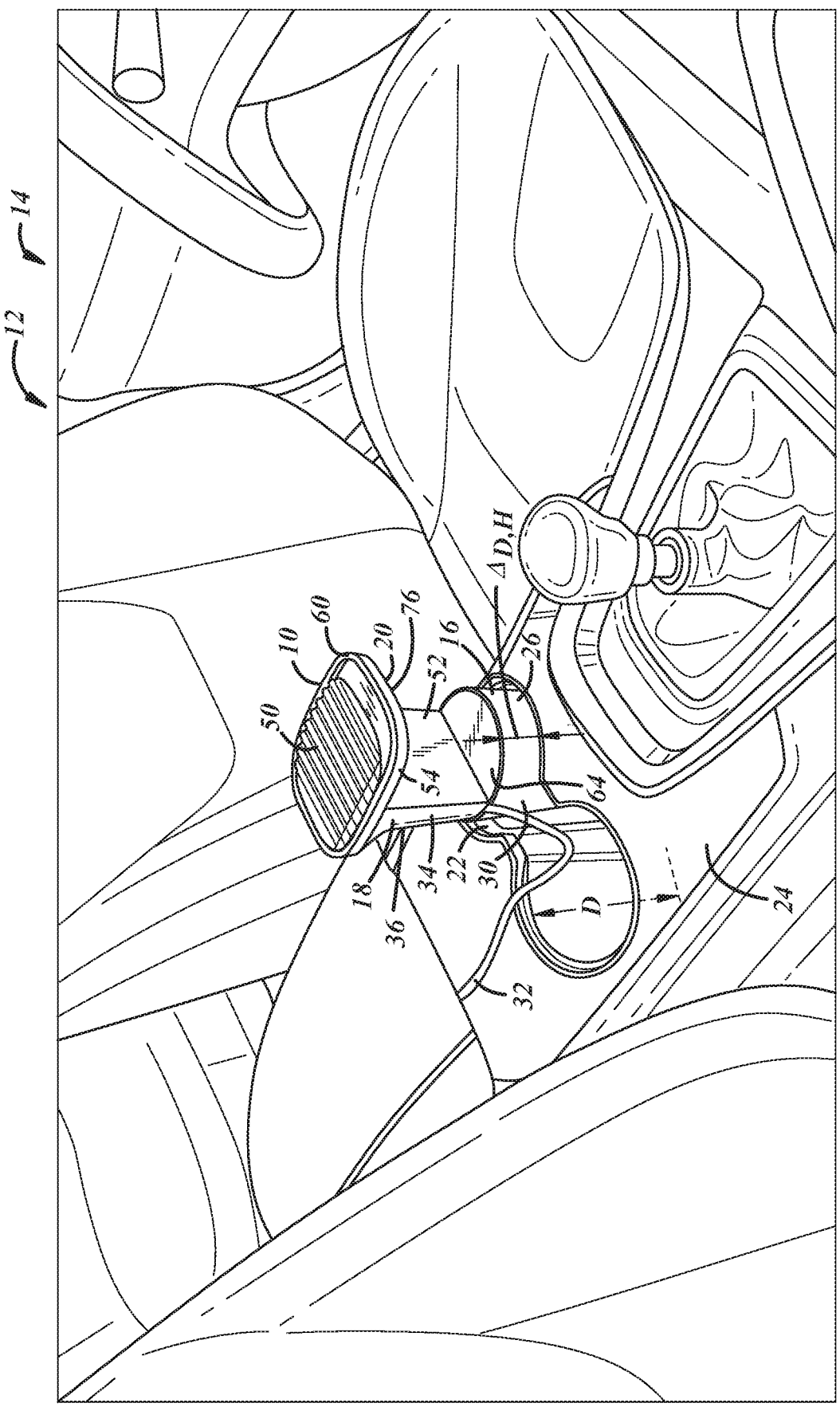
FIG. 1 illustrates a portion of a vehicle interior and a sanitizing cup according to one embodiment.

FIG. 1 illustrates a sanitizing cup 10 within an interior passenger cabin 12 of a vehicle 14. The sanitizing cup 10 in this embodiment provides an integrated solution for disinfecting within the passenger cabin 12, as it includes a cup base 16 with a sanitizing compartment 18 and a hand sanitizer dispenser 20 extending from the cup base. The sanitizing cup 10 in the illustrated embodiment is sized to fit within a cupholder 22 of the vehicle 14. The cupholder 22 is located in the center console panel 24, but it is possible to locate the sanitizing cup 10 in other cupholders within the vehicle 14, such as in door panel cupholders, rear cupholders, etc. Further, in the illustrated embodiments, the sanitizing cup 10 is a standalone device that can be moved to different locations within the passenger cabin 12. This can be beneficial in some implementations, such as when the cup 10 is sold as an aftermarket component. Moreover, it is possible for the sanitizing cup 10 to be used in other non-vehicle-based environments. In some vehicle-based embodiments, it is possible for the cup base 16 to be an integral part or integrally built into the center console panel 24, a door panel, or another interior panel of the vehicle 14, such as a dash panel, rear armrest panel, etc. In such an embodiment (see e.g., FIG. 4), the cup base 16 could either be wholly located within the panel or may extend partially from the panel.

With reference to FIGS. 1 and 2, the cup base 16 serves as a structural foundation for the various components of the sanitizing cup 10. In the illustrated embodiments, the cup base 16 is a circular cylinder storage compartment 26 that is configured to be at least partially nested within the vehicle cupholder 22. The cup base 16 has a bottom surface 28 and a circular cylindrical sidewall 30 that extends up from the bottom surface. The circular cylindrical sidewall 30 can be tapered as shown, such that a diameter of the bottom surface 28 is smaller than a diameter of the cup base 16 at the other end of the cylindrical sidewall 30. This configuration can help with nesting within the cupholder 22. The height of the cup base 16 is designed to be just greater than the depth D of the cupholder 22 (see FIG. 2 for the height H of the cup base 16 and FIG. 1 for the depth of the cupholder 22). This results in a differential $\Delta_{D,H}$ that provides sufficient clearance for the hand sanitizer dispenser 20 to be located in a more optimal location with respect to the interior panel 24. The depth D of the cupholder 22 may be about 60 mm 100 mm, and the height H of the cup base 16 can be proportional such that the resulting differential $\Delta_{D,H}$ is about 2 mm-20 mm. Other sizes and shapes for the cup base 16 are certainly possible.

The cup base 16 and its circular cylindrical storage compartment 26 can house various parts of the sanitizing cup 10, such as a power cord 32 or other power supply, and various subcomponents of the sanitizing compartment 18 and the hand sanitizer dispenser 20 which are detailed further below. In embodiments in which the sanitizing cup 10 is integrally built into the vehicle interior panel 24, the cup base 16 may not have a separate storage compartment 26, and instead, the various subcomponents can be stored beneath the panel. The power cord 32 in this embodiment is a USB charger, which can be easily plugged into a USB adapter in the passenger cabin 14. Other power sources may be used instead, such as a vehicle battery if the cup base 16 is integrated into the panel, a cigarette lighter adapter, or batteries within the cup base storage compartment 26 itself, to cite a few examples.

The outer surfaces of the cup base 16, the sanitizing compartment 18, and the hand sanitizer dispenser 20 can be made of any operable material, but advantageously, the material is rigid and nonporous, allowing for easy cleaning and providing a more anti-bacterial surface. Example nonporous materials include varnished wood, acrylic, PVC, or another rigid plastic. The various walls and surfaces of the sanitizing cup 10 may comprise a single sheet or layer of material, or in some embodiments, may have a multi-layer structure (e.g., dual walled structure, a coated surface, etc.). In some implementations, part of the cup base 16 may be light-transmissive, meaning that at least some light can pass through the sidewall 30. Light transmissive may include any non-opaque configuration, such as one that is transparent, translucent, semi-transparent, semi-translucent, etc. Having a light-transmissive sidewall 30 may allow a user to see the amount of hand sanitizer remaining in a hand sanitizer reservoir located in the cup base 16. A coating or the like that helps to reduce the transmission or bacteria and/or viruses may also be used. Hygienic configurations (e.g., smoother surfaces, less grooves, etc.) can be beneficial as well. Other example materials and configurations for the cup base 16, the sanitizing compartment 18, and the hand sanitizer dispenser 20 are certainly possible.

The sanitizing compartment 18 extends at least partially from the cup base 16 and has a sanitizing area 34 that is at least partially enclosed by a first compartment wall or sidewall 36 and a second compartment wall or bottom wall 38. The sanitizing area 34 is configured to store an object to be sanitized. In the illustrated embodiments, the object to be sanitized is advantageously a mask 40 as shown in FIG. 2, yet it is possible to use the sanitizing compartment 18 to sanitize other objects, such as a user's keys, phone, etc. depending on the desired implementation. The curved compartment sidewall 36 creates a sanitizing area 34 that is at least partially U-shaped along the sidewall. This shaped sanitizing area 34, that is either fully U-shaped or partially U-shaped (e.g., a semi-circular cylinder) can better conform to the shape of the mask 40 and provides a more efficiently spaced storage area for the mask within the vehicle 14.

The sanitizing compartment 18 includes a sanitizing device 42 that sanitizes an object stored within the sanitizing area 34. The sanitizing device 42 serves to actively disinfect the object stored in the sanitizing area 34. The sanitizing device 42 advantageously is a UVC light source 44; however, other disinfection systems and types are certainly possible. For example, the sanitizing device 42 may be a disinfecting spray that is dispersed within the sanitizing area 34 when a sanitization cycle is initiated. In another example, hydrogen peroxide fogging and/or heat treatment capabilities can be implemented to help bolster disinfection potential.

Figure 4:
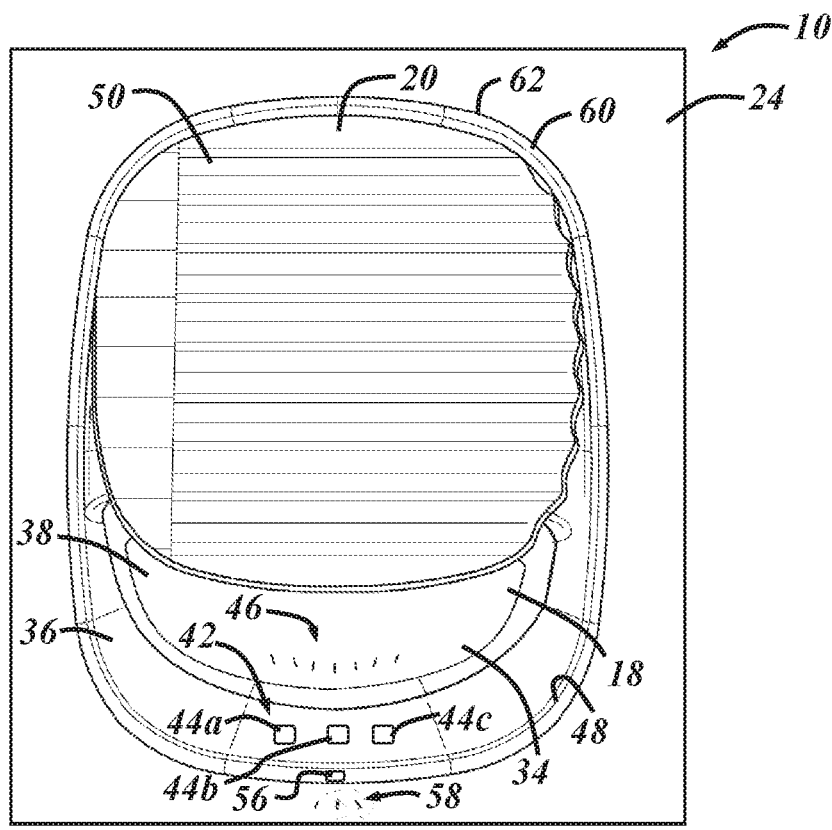
FIG. 4 illustrates the inside of a sanitizing compartment of a sanitizing cup according to another embodiment.

With particular reference to FIGS. 3 and 4, the illustrated embodiments include a UVC light source 44 as the sanitizing device 42 for the sanitizing compartment 18. The UVC light source 44 can enable deep, automized disinfection of object surfaces. The UVC light source 44 emits UVC light 46, and direct exposure to the UVC light can destroy a pathogen's DNA. The amount of disinfection achieved by the UVC light 46 is at least partially dependent on the target surface location and light source 44. The UVC light source 44 can consist of one or more local sources, such as UVC LEDs which provide more localized surface disinfection within the sanitizing compartment 18.

The UVC light source 44 may be located directly on one or both of the compartment walls 36, 38, or the light source 44 may include one or more lenses/diffusers located on one or both of the compartment walls 36, 38 with LEDs or the like located behind the lenses/diffusers. FIG. 3 shows the UVC light source 44 located on the bottom wall 38. In this orientation, the UVC light 46 is directed more toward an opening 48 in the sanitizing compartment 18. The compartment opening 48 provides access to the sanitizing area 34, and to prevent UVC light 46 from undesirably escaping through the opening 48, a cup lid 50 can be provided. FIG. 4 shows an alternate or additional configuration for the UVC light source 44 in which the UVC light 46 illuminates from the sidewall 36 from each individual UVC LED light source 44a-c toward a sanitizer backing wall 52 opposite the sidewall. In the embodiments illustrated in FIGS. 3 and 4, the UVC light source 44 is configured to form a U-shaped light distribution 54 coming from the respective compartment wall 36, 38, either by virtue of the shape of the light source itself (e.g., FIG. 3) or by virtue of the shape of the wall from which the light 46 initially propagates (e.g., FIG. 4). Other light locations, types, arrangements, etc. are feasible.

When using the UVC light source 44 as the sanitizing device 42, various subcomponents can be included or housed within the storage compartment 26 of the cup base 16, including but not limited to, a PCB and electronics, a small fan, and a motor. Other features to enhance performance of the UVC light source 44 can also be included, such as a heat sink to assist with thermal control and features within the sanitizing area 34 to promote particular light distribution patterns. For example, one or more of the walls 36, 38, 52, as well as an underside of the lid 50, may be made from a reflective material or may be coated with a metallic coating to promote reflection within the sanitizing area 34. This can help promote disinfection by encouraging additional reflectance of the light 46.

The UVC light source 44 and the implementation of a sanitization cycle, to sanitize the mask 40 for example, can be controlled by object detection, automation (e.g., time-based or vehicle status-based), manual control (e.g., via a button or closing the lid 50), and/or remote control. The length of a sanitization cycle can be a set parameter which is dependent on the qualities of the light source 44, or it can be user controlled. According to one embodiment, a sanitization cycle is implemented when a user closes the lid 50. FIG. 1 illustrates the sanitizing cup 10 in a closed state in which the cup lid 50 is situated over the opening 48 to the sanitizing compartment 18. Moving the lid 50 to this closed state from an open state, such as the state illustrated in FIG. 2 in which the cup lid is located over an overhanging dispensing wall 54, can initiate a sanitization cycle. When the sanitization cycle is complete, the lid 50 may be configured to automatically transition from the closed state to the open state so that a user can easily access the disinfected object 40 in the sanitizing area 34. This lid opening transition provides an easily perceivable indication that the sanitization cycle is complete. Another way to indicate that a sanitization cycle has been completed is illustrated in FIG. 4. The sanitizing cup 10 in FIG. 4 includes a sanitization status indicator 56. The sanitization status indicator 56 can display light 58 to a user indicating different stages with respect to the sanitization cycle, for example. In another example, the sanitization status indicator 56 may be configured to emit a single color light to indicate that a sanitization cycle is complete. The sanitization status indicator 56 may include an RGB LED or some other multi-colored light source to show various colors depending on a corresponding stage of the sanitization cycle (e.g., white light for lid 50 in the open state, red light for sanitization in progress, green light for indicating that the sanitization cycle has ended, etc.). Other ways to initiate and communicate information regarding the sanitization cycle are certainly possible.

The cup lid 50 at least partially encloses the sanitizing area 34, which can help keep UVC light 46 around the object to be sanitized during the sanitization cycle. The cup lid 50 can be slidably disposed within the rim 60 along a track 62, as illustrated in FIG. 3. Other lid configurations include a hinged configuration, a folding configuration, or a rolling tambor style configuration, to cite a few examples. Movement of the lid 50 along the track 62 or along grooves or the like near the rim 60 may be user controlled, motor controlled, or both, and as described above, movement of the lid 50 between the open state and the closed state may be at least partially dependent on a stage of the sanitization cycle. Magnets can be used at locations nearest the open and closed states to help guide the lid 50 more easily into the desired position.

In addition to the sanitizing compartment 18, the sanitizing cup 10 includes an integrated hand sanitizer dispenser 20. The hand sanitizer dispenser 20 includes the sanitizer backing wall 52, the overhanging dispensing wall 54, and a drip wall 64. The sanitizer backing wall 52 serves as one of the compartment walls of the sanitizing compartment 18, and the overhanging dispensing wall 54 includes the opening 48 into the sanitizing area 34. The hand sanitizer dispenser 20 thus extends from both the cup base 16 and the sanitizing compartment 18 in this embodiment. Further, the drip wall 64 serves to at least partially cover the storage compartment 26 in the cup base 16. This shared configuration can more efficiently utilize in-vehicle space for both disinfecting a user's hands and an object of the user in a more compact device. The sanitizer backing wall 52, the overhanging dispensing wall 54, and the drip wall 64 together create an alcove area where a user's hand can be located and receive hand sanitizer. However, the hand sanitizer dispenser 20 can be alternately configured. For example, the hand sanitizer dispenser 20 may house a manual pump for the dispensing of hand sanitizer instead of the automatic dispenser described herein. In yet another embodiment, the sanitizer may be dispensed from the sanitizer backing wall 52 instead of the overhanging dispensing wall 54. A recessed area in the drip wall 64 can act as a sanitizer receiver for misuses or over-dispensed sanitizer. Other configurations are possible.

As shown schematically in FIG. 3, the hand sanitizer dispenser 20 includes a reservoir 66 for storing hand sanitizer, such as an alcohol-based sanitizer, with a pump 68 and nozzle 70 for dispensing the sanitizer. The reservoir 66 for storing the sanitizer is located in the storage compartment 26 of the cup base 16. This arrangement, particularly in embodiments in which the cup base 16 is removable, allows for a user to easily refill the reservoir 66 when more sanitizer is needed. The reservoir 66 and/or the cup base 16 may be light-transmissive in order to visibly display the remaining level of sanitizer. Sanitizer is pumped from the reservoir 66 via a pump 68 and one or more conduits 72. To provide space for the alcove defined by the sanitizer backing wall 52, the overhanging dispensing wall 54, and the drip wall 64, one or more conduits 72 may be used to route sanitizer to a more optimal dispensing location.

Figure 5:
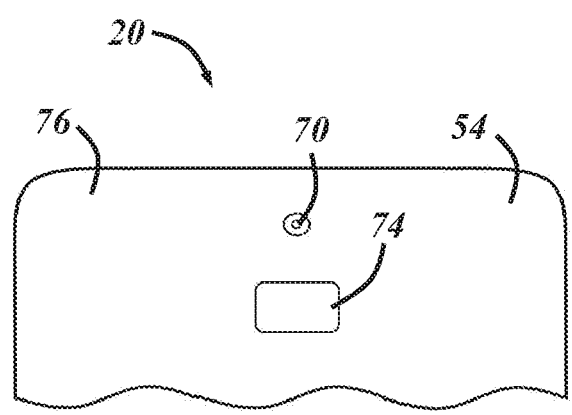
FIG. 5 is a partial view of an overhanging dispensing wall of a sanitizing cup, such as the sanitizing cup shown in FIGS. 1-4.

In the illustrated embodiment, the hand sanitizer dispenser 20 is an automatic hydroalcoholic gel dispenser situated for easy use by the driver or another passenger of the vehicle 14. In other embodiments, the hand sanitizer dispenser is a passive, manually operated dispenser. In the illustrated embodiments, the hand sanitizer dispenser 20 has power-based features such as automatic hand detection which triggers automatic dispensing. Accordingly, with reference to FIG. 5, a sensor 74 (e.g., an infrared sensor) is included on an underside 76 of the overhanging dispensing wall 54 to detect hand presence and trigger sanitizer dispensing. In some embodiments, the sensor 74 may be located in a different location, such as on the sanitizer backing wall 52. Upon ingress into the vehicle 14, the driver, for example, can easily remove his or her mask 40, sanitize it in the sanitizing compartment 18, and sanitize his or her hands before contacting various portions of the interior cabin 12.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all the following: "A"; "B"; "C"; "A and B"; "A and C"; "B and C"; and "A, B, and C."

The invention claimed is:

1. A sanitizing cup, comprising:
    a cup base;
    a sanitizing compartment extending at least partially from the cup base, the sanitizing compartment having a sanitizing area at least partially enclosed by a compartment wall, wherein the sanitizing area is configured to store an object to be sanitized; and
    a hand sanitizer dispenser extending at least partially from the cup base, the sanitizing compartment, or from both the cup base and the sanitizing compartment, wherein a reservoir for hand sanitizer is located in the cup base and the sanitizing compartment is located at least partially on top of the reservoir in the cup base.

2. The sanitizing cup of claim 1, wherein the sanitizing compartment includes an ultraviolet-C (UVC) light source.

3. The sanitizing cup of claim 2, wherein the ultraviolet-C (UVC) light source is configured to form a U-shaped light distribution coming from the compartment wall.

4. The sanitizing cup of claim 3, wherein the compartment wall is a sidewall so light from the ultraviolet-C (UVC) light source is configured to be directed more toward a sanitizer backing wall opposite the sidewall.

5. The sanitizing cup of claim 3, wherein the compartment wall is a bottom wall so light from the ultraviolet-C (UVC) light source is configured to be directed more toward an opening in the sanitizing compartment opposite the bottom wall.

6. The sanitizing cup of claim 1, wherein the sanitizing area is at least partially U-shaped and configured to store a mask as the object to be sanitized.

7. The sanitizing cup of claim 1, wherein a height of the cup base is configured to be greater than a depth of a vehicle cup holder.

8. The sanitizing cup of claim 1, wherein the cup base is integrally built into an interior panel for a vehicle.

9. The sanitizing cup of claim 1, wherein the hand sanitizer dispenser includes a drip wall, a sanitizer backing wall, and an overhanging dispensing wall.

10. The sanitizing cup of claim 9, wherein a nozzle and a sensor are located on the overhanging dispensing wall, and the sensor is configured to detect a user's hand and dispense sanitizer via the nozzle.

11. The sanitizing cup of claim 1, further comprising a sanitization status indicator configured to indicate a sanitizing status relating to the object to be sanitized.

12. The sanitizing cup of claim 1, further comprising a cup lid configured to at least partially enclose the sanitizing area.

13. A sanitizing cup, comprising:
    a cup base;
    a sanitizing compartment extending at least partially from the cup base, the sanitizing compartment having a sanitizing area at least partially enclosed by a compartment wall, wherein the sanitizing area is configured to store an object to be sanitized;
    a hand sanitizer dispenser extending at least partially from the cup base, the sanitizing compartment, or from both the cup base and the sanitizing compartment; and
    a cup lid configured to at least partially enclose the sanitizing area, wherein the cup lid is configured to slide between an open state in which the cup lid is situated over an overhanging dispensing wall and a closed state in which the cup lid is situated over an opening in the sanitizing compartment.

14. The sanitizing cup of claim 13, wherein the cup lid is configured to automatically transition between the open state and the closed state upon completion of a sanitization cycle.

\* \* \* \* \*